United States Patent
Bonnet et al.

(10) Patent No.: US 6,832,914 B1
(45) Date of Patent: Dec. 21, 2004

(54) PREFORM ALLOWING THE PRODUCTION OF PERSONALIZED ORTHONDONTIC APPARATUSES FOLLOWING DEFORMATION, THE APPARATUSES OBTAINED AND THE PROCESS FOR THEIR PRODUCTION

(76) Inventors: Maïwenn Bonnet, 16, rue Deparcieux, 75014, Paris (FR); François Bonnet, 1, rue des Alouettes, 69680, Chassieu (FR); Bruno Bonnet, 12, rue Danton, 94270, Le Kremlin Bicetre (FR)

( * ) Notice: Subject to any disclaimer, the term of this patent is extended or adjusted under 35 U.S.C. 154(b) by 0 days.

(21) Appl. No.: 09/423,858
(22) PCT Filed: May 15, 1998
(86) PCT No.: PCT/FR98/00984
§ 371 (c)(1),
(2), (4) Date: Feb. 25, 2000
(87) PCT Pub. No.: WO98/51472
PCT Pub. Date: Nov. 19, 1998

(30) Foreign Application Priority Data

May 15, 1997  (FR) .............................................. 97 06082

(51) Int. Cl.⁷ .............................. A61C 7/00; B29C 49/00
(52) U.S. Cl. .............................. 433/213; 433/6; 264/573
(58) Field of Search .............................. 433/6, 18, 24, 433/213, 229; 264/523, 573

(56) References Cited

U.S. PATENT DOCUMENTS

| 1,896,123 A | * | 2/1933 | Schweitzer | .................. 264/523 |
| 2,317,763 A | * | 4/1943 | Hall | .......................... 264/523 |
| 4,079,111 A | * | 3/1978 | Uhlig | ............................ 264/89 |
| 4,264,558 A | * | 4/1981 | Jacobsen | ..................... 264/523 |
| 4,320,083 A | * | 3/1982 | Jakobsen | ..................... 264/523 |
| 4,391,861 A | * | 7/1983 | Nilsson | ...................... 264/523 |
| 4,785,948 A | * | 11/1988 | Strassheimer | ............... 215/1 C |
| 4,798,534 A | * | 1/1989 | Breads | ........................ 433/213 |
| 5,158,817 A | * | 10/1992 | Krishnakumar | .......... 428/36.92 |

FOREIGN PATENT DOCUMENTS

DE          36 10349 A1     10/1987

OTHER PUBLICATIONS

M. Amoric, "Gouttieres Orthodontiques et Orthopediques Thermoformees", 1993.

* cited by examiner

Primary Examiner—Ralph A. Lewis
(74) Attorney, Agent, or Firm—Arent Fox PLLC

(57) ABSTRACT

This invention pertains to the area of orthodontic apparatuses, particularly those that have been precisely adapted to the specific morphology of each patient.

The invention proposes a preform dissimilar to a plate; the form of which allows it to expand within a mold that reproduces a patient's morphology; it may be mass produced and easily adapted by the practitioner or prosthesis maker to each patient's morphology as well as orthodontic or dento-facial orthopedic apparatuses obtained from this preform and their manufacture process.

Such apparatuses are, for example, Bonnet's N.L.E. (Night-time Lingual Envelopes—Enveloppe Linguale Nocturne) or any apparatus presenting a general hollow body form, possibly with one or more openings, varying thickness, and which, because of this specific geometry, cannot be produced from a model in the form of a flat plate.

31 Claims, 8 Drawing Sheets

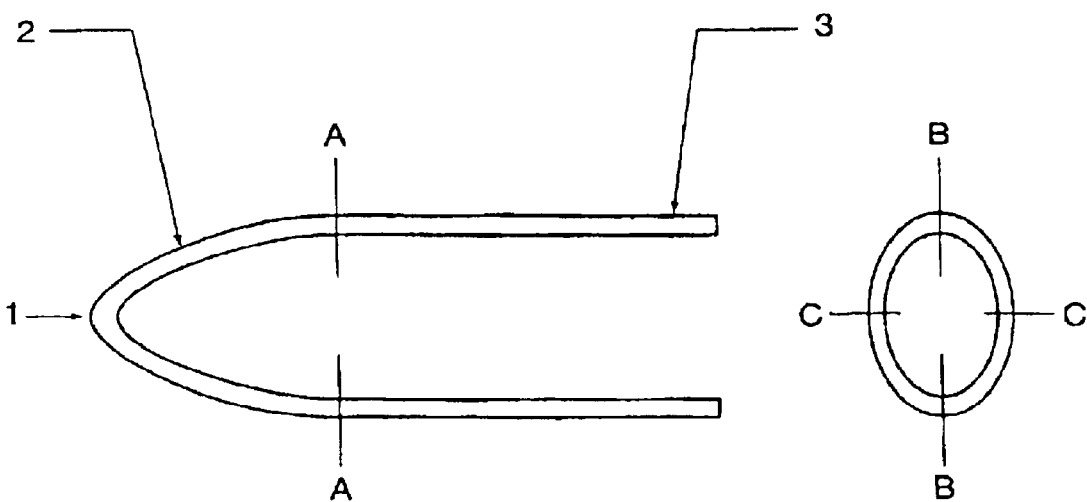
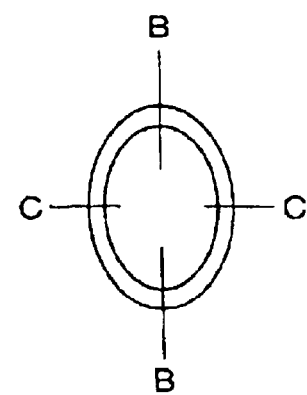
Fig. 1B          Fig. 1A
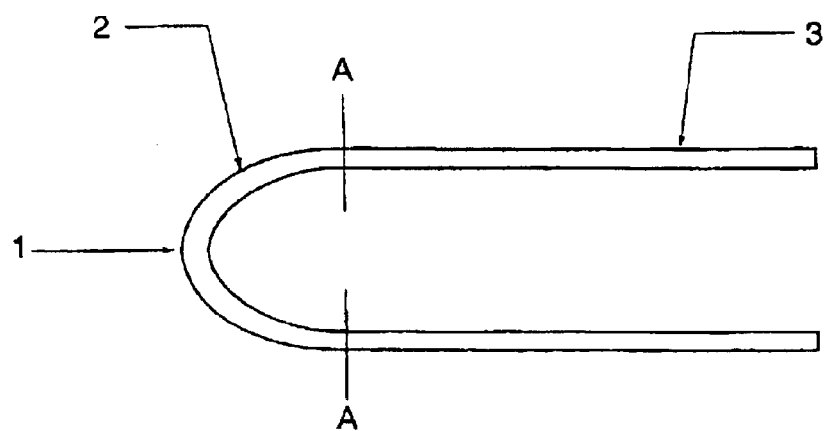
Fig. 1C

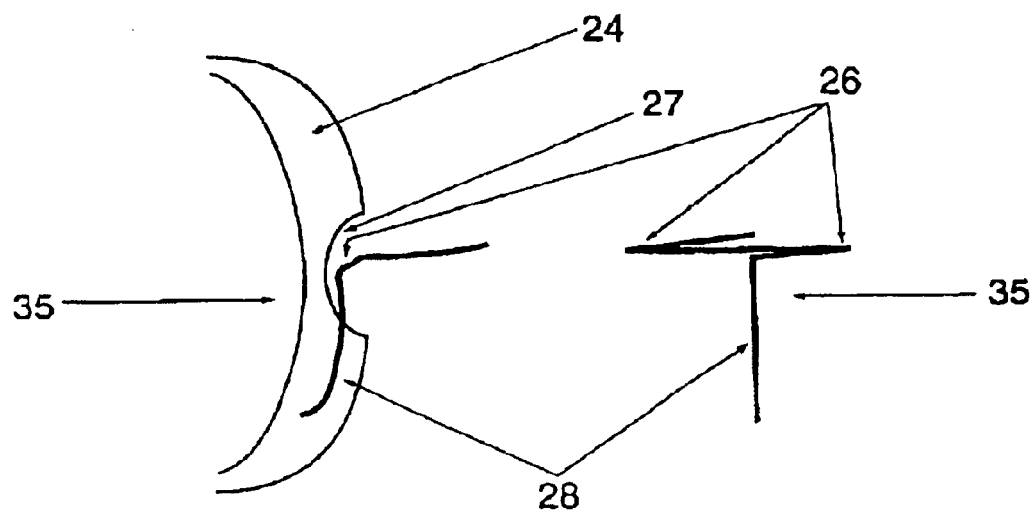
Fig. 8A    Fig. 8B
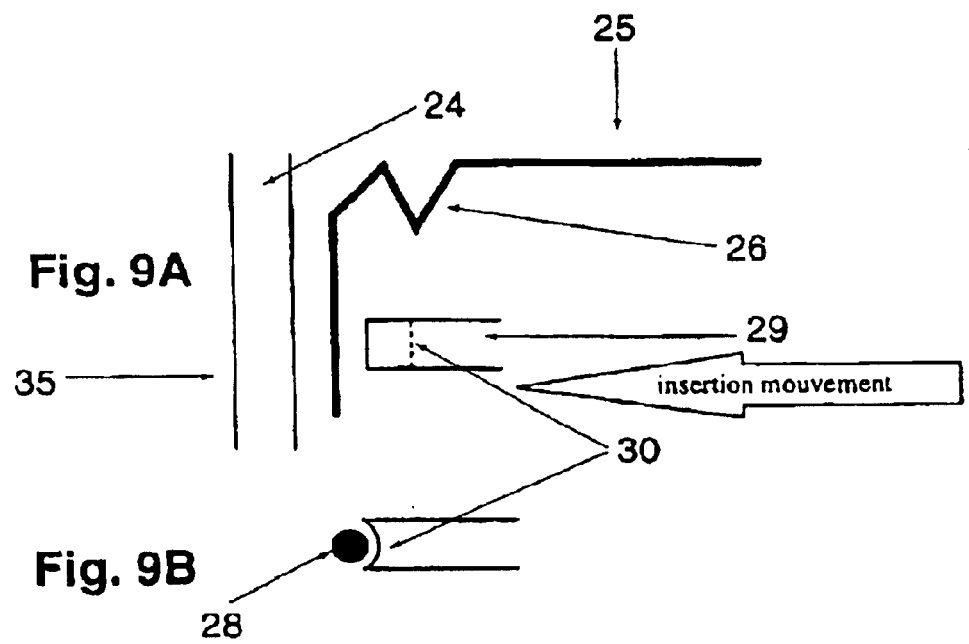
Fig. 9A
Fig. 9B

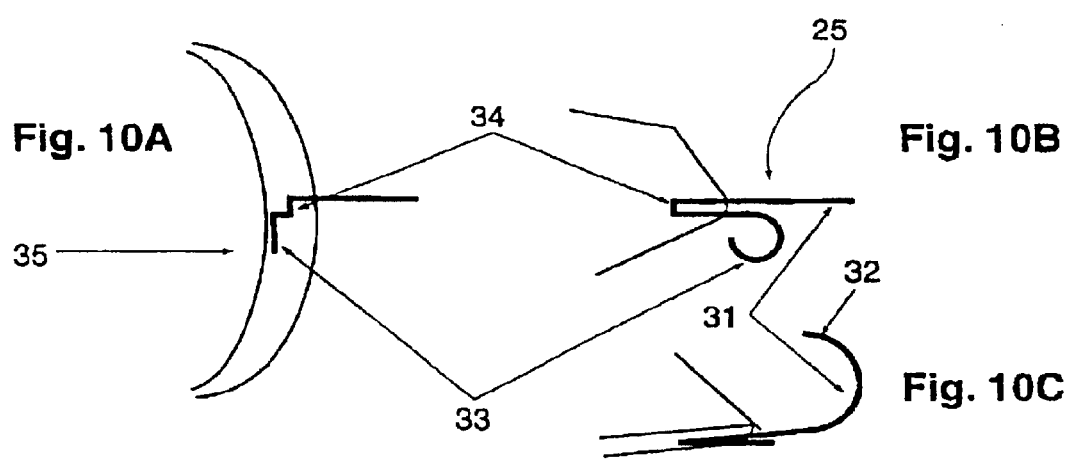

PREFORM ALLOWING THE PRODUCTION OF PERSONALIZED ORTHONDONTIC APPARATUSES FOLLOWING DEFORMATION, THE APPARATUSES OBTAINED AND THE PROCESS FOR THEIR PRODUCTION

CROSS-REFERENCE TO RELATED APPLICATION

This application is related to International Application No. PCT/FR98/00984, filed May 15, 1998, the entire specification of which is incorporated herewith by reference.

FIELD OF INVENTION

This invention concerns the orthodontic or dento-facial orthopedic apparatus sector, particularly those which are precisely adapted to the specific morphology of each patient.

More particularly, it concerns all orthodontic or dento-facial orthopedic apparatuses having a general hollow body which may have one or more openings, variable thickness, and which, due to this particular geometry, cannot be produced from a flat plate.

BACKGROUND OF THE INVENTION

Such apparatuses, which may be removable, may be those intended to maintain a patient's tongue in a given volume, particularly Bonnet's Nighttime Lingual Envelope or N.L.E.

More generally, the invention concerns apparatuses which must necessarily be adapted very precisely to each patient or user in order to fulfill their function and which cannot be manufactured based on a blank in the form of a flat plate due to their final complex shape (open hollow body, variable thicknesses which cannot be obtained by simply shaping a plate, etc.). By contrast, these apparatuses are produced starting from a blank or preform whose shape permits it to be expanded in a mold that reproduces the patient's morphology. This preform has the general shape of a three dimensional hollow body, more particularly, a hollow, tubular or approximately tubular form, more particularly still, a hollow, tubular or approximately tubular form which is cut on the upper anterior part to form an opening.

Traditionally, such apparatuses are tailor-made, created in a laboratory and therefore, piecemeal, starting from formed molds based on research models which have themselves been formed based on an impression or impressions made in the practitioners office by the same.

Several apparatuses are generally necessary during treatment, to follow changes in the patient's morphology. The need to produce a new apparatus during treatment may also come from the need to move the fastening hooks due to a change in the environment (for example, with the appearance of wisdom teeth or with shifting of teeth). Each time a cast must be taken to produce a model, then a mold, and then the final apparatus must be produced.

More specifically, the traditional process for manufacture is a contact molding process. It occurs in four steps:

Construction of the Mold

The practitioner makes a casting of the upper maxilla and possibly a casting of the lower maxilla of his patient, most often with alginates due to their rapid polymerization and biocompatibility properties. These castings act as a base for the production of a model in one or two parts which is most often in plaster, completed using wax that sticks easily and/or is easily deformed. This requires that the technician have great technical proficiency, integrating brief perceptions, dexterity, and experience. The technician, also using wax, positions the fastening systems (or fastening hooks and pins), generally metal wires which shall then be duplicate molded and shall perform the fastening function of the completed apparatus in the patient's mouth as well as any other additional necessary piece.

Contact Molding

A resin with two components is used, a solid powder and a fluid, adapted to contact molding of traditional orthodontic pieces. Work is conducted with successive passes of dampening by the liquid using a pipette and/or dusting with the solid.

However, the shape of the hollow body with variable thickness in certain apparatuses such as the N.L.E. by Bonnet results in special difficulties during production since the different areas of the apparatus have quite varied orientations and curvature radii. Therefore, the technician is confronted with several difficulties.

(i) A compromise must be found between passes that are too liquid or too thin or of such small surface that multiples are needed, thus lengthening the operating time, and passes which are too thick or too pasty which creates irregular upper thicknesses that will then need grinding.

(ii) It is difficult to estimate or measure the deposited thicknesses to inspect ones work as it progresses, (iii) A choice must be made between molding of all passes in a single operation lasting several minutes or up to a quarter of an hour followed by a single final polymerization or molding with several very brief operations each lasting approximately a minute with as many intermediate polymerization phases in an autoclave pressurized above atmospheric pressure (otherwise gas bubbles arise deterring from the piece's final appearance). In the first case, one obtains a piece having irregular transparency and which is little flattering, in the second case, the production time, and therefore the cost are noticeably higher.

Mold Ejection and Finishing

The blank is ejected from the mold, then finishing takes place using machining and grinding. The shape of the preform being somewhat removed from the final piece, finishing is a long and delicate operation generating noise and dust. Since this pollution is incompatible with a dentist's office, finishing must take place in an area with specific equipment, namely, for example, a suction hood.

There are variations in which the teeth and gums part of the lower maxilla model are used complementing the upper maxilla model. A filler material (for example, plaster) is used to complete the missing part in order to obtain a complete mold. In this case, the mold is completely exterior to the piece to be molded; the general accessibility and visibility are not as poor as in the preceding variation.

The apparatus is then equipped with hooks in order to be attached to the patient's mouth. Currently, there are mainly two types of hooks or claws or fastening systems, hereafter fastening hooks, (Step 1) used depending on the morphology and the dental age of the patient, in general made of stainless steel orthodontic wires:

Lateral Hooks (Generally Symmetrical, Totaling 2)

They are used especially for young children. They are anchored in the apparatus at one end which is inserted in the lateral wall of the apparatus, the other end being inserted elastically into a diastema to attach the apparatus to the mouth. They are generally cold-formed using the Sahar method, meaning that the beginning of the emerged part has a zigzag shape such that it may be deformed by the practitioner to adjust the tightness of the anchoring when it is first placed in the mouth and on the following visits depending on the changes in the patient's oral environment, all without changing the anchoring, that is, the position of the part of the hook included in the apparatus. In the thickness of the outside wall of the apparatus, a hollow is reserved to lodge this zigzag whose shape changes during the apparatus' life.

The Posterior Hooks (Generally Symmetrical, Totaling 2)

They are anchored in the apparatus such that the wire exits at the rear of the apparatus approximately in the horizontal occlusion plane. The wire then generally follows the contours of the teeth which are farthest back (for example, the 6 year tooth or the 12 year tooth), then it comes to exert pressure from the outside on the tube of a ring. It is formed in such a way that with the slight symmetrical forces of the two posterior right and left hooks pressing upward and outward in reaction to the apparatus it is kept in position against the palate.

This production method offers certain inconveniences. In effect, production costs are high (made to order), the appearance and quality of the product are often insufficient (manual), at times, considerable finishing is needed, delays are excessive. Furthermore, the alginate cast is destroyed when the plaster model is released from the mold. Therefore, the model must not be damaged so that the patient does not have to undergo the procedure again. So, this plaster model is very fragile. It must be handled all the more delicately, which requires more care and time. Finally, the procedure generates noise, dust, and odors (solvents, etc.).

Attempts at thermoforming have been made in order to be freed from some of the disadvantages linked to the traditional procedure. The thermoforming technique is widely used for producing orthodontic apparatuses and is described in many general works.

In the domain of orthodontics, the document DE 36 10 349 may be mentioned. It describes a process and mechanism to create an orthodontic apparatus. The base material is present in the form of a plastic film with constant thickness, maintained by film supports which undergo deformation through the addition of heat and applied pressure, until a model is created based on casting taken directly from the patient.

Michel AMORIC's publication: "Gouttieres orthodontiques et orthopédiques thermoformées" *Thermoformed orthodontic and orthopedic splints,* 1993, Editions SID can also be mentioned. The principle behind this technique is that one uses a flat plate as a base material with a constant thickness. Starting with a traditionally produced mold the plate is deformed so as to obtain an apparatus having an appropriate shape.

Not all apparatuses can be obtained by this method. In particular, this method is not efficient for apparatuses having a hollow body and variable thickness. The stretching that the plate must withstand in these specific cases is considerable and therefore difficult to obtain without tearing. Most of all, thicknesses cannot be controlled since they are simply dependent on the stretching necessary to obtain the desired shape and are therefore irregular since not all areas are stretched in the same manner. This technique is therefore not appropriate for a certain number of cases.

The variant consisting in the use of a two part apparatus, that is, two base plates yielding two half-apparatuses that are assembled is also not adequate. It allows a decrease in the stretching undergone by the plates, and therefore in the risks of ripping and the problems of too irregular thicknesses, but the problem is in part displaced to the assembly of the two half-apparatuses obtained. In effect, the difficulty lies in the precision and solidity of the glued or soldered assembly, inasmuch as one must also install in this assembly area the fastening hooks for the fastening of the apparatus in the patient's mouth.

The thermoforming methods used up to present day therefore do not allow the production of apparatuses with hollow bodies and variable thicknesses and the risks of damaging the sole plaster mold are significant.

The invention allows these problems to be solved by proposing a three dimensional apparatus that can be produced in series, thereby at low cost; this apparatus is called a preform. This preform is different from a flat plate and has a general shape permitting it to expand in a mold that reproduces the patient's morphology. This preform has the general shape of a three-dimensional hollow body, more particularly, a hollow, tubular or approximately tubular form, more particularly still, a hollow, tubular or approximately tubular form which is cut on the upper anterior part to form an opening. Said preform may then be perfectly adapted to each patient in the practitioner's office or in the prosthesis maker's laboratory by a deformation process including expansion that is quick and easy to implement, in a mold constructed starting with a plaster model, without any risk for said plaster model. It allows a functional apparatus to be obtained which cannot be obtained by traditional thermoforming starting with a flat plate.

The term "technician" shall refer to the person transforming the preform into a functional apparatus, whether this is the practitioner in the office or the prosthesis maker in the laboratory.

More specifically, this preform is manufactured in a biocompatible material due to the at times prolonged contact with a human cavity [the mouth]. It must, in this respect, meet current applicable standards. It may be a thermosetting or thermoplastic type of plastic material deformable through expansion and obtained, for example, by injection or any other appropriate industrial process (first stage processing), and presenting a three dimensional shape such that its deformation easily allows for the creation of the final apparatus adapted to each patient. This deformation or second stage processing, which includes expansion, is performed rapidly and easily by the technician according to the patient's morphology.

In this description, expansion of the preform means the volumetric development or deformation of the preform.

The invention has merit in that it has removed the disadvantages related to the necessary production and individualized adaptation of an orthodontic apparatus by permitting low-cost series manufacturing of a preform which shall then be easily adaptable to the patient by the practitioner or prosthesis maker in order to obtain, after finishing, a functional apparatus with a hollow body of varying thicknesses that would not be possible with the simple deformation of a flat plate, and, in some variants (particularly if thermoplastic material is used) is capable of being equipped with fastening hooks in the mouth by a process which allows changes in anchoring points.

The production cost is therefore lower; the delays are shorter; the process is clean (without dust, noise, or odor) and simple to implement, without risk to the plaster model, and facilitates the technician's work.

The shape of the preform is defined while taking into account mean deformations to which it shall be subject during second stage processing—for example, reduction of thickness and width variables of the walls, according to the desired functional apparatus. It is therefore possible to envisage a preform for such an apparatus and for patients of a given size or gender or age. Thus, series production of the preform is allowed even while limiting the deformations that it shall undergo, thereby the lengths and complexity of the second stage processing.

In one variation, it is also possible to imagine having the preform manufactured and delivered to the technician in a developed flattened shape, thus generally shaped in two dimensions and no longer in three dimensions. This is called a developed preform. Such a case shall be detailed later making reference to figures. The developed preform is then given a volume by the technician by rolling or bending around an appropriate gauge which may be a controlled expansion core to create the preform as such. Thus, the production cost is decreased, as is the volume of the preform manufactured in series which, here, is a developed preform. Furthermore, this structure in two dimensions facilitates certain manipulations by the technicians (preparation of an opening, etc.). However, the possibility to define the thickness at each point of the preform is retained since the developed preform may itself be of a variable thickness according to each area. The connection (cross-section) to recreate the hollow body is located in the least deformed area during expansion, for example the bow of a slide in the case of Bonnet's N.L.E. The weld is performed by hand using pressure (for example, a self-adhesive effect, by application of a solvent or glue adapted to the material of the developed preform) such that it then resists expansion.

The second stage process is dependent on the plastic material used. If thermoplastic plastic materials are used, the second stage process may be carried out with techniques belonging to blowing, thermoforming, injection blow molding, even mechanical means or any other appropriate means. If thermosetting material is used, the second stage process may be carried out with techniques similar to compression, dry bag molding, vacuum molding, preforming on a diaphragm, or any other appropriate means.

This second stage process shall be performed by the technician, that is to say, by the practitioner, in his office or by the prosthesis maker in his laboratory, rapidly and easily by a "clean" process, that is to say, without dust, noise or odor, within very short time frames and in conditions that allow perfect adaptation to the patient's morphology.

Furthermore, the different apparatuses necessary during treatment due to changes in the patient's morphology can be produced successively based on the first apparatus produced from a preform. Thus, the first apparatus shall become the preform for the second apparatus which shall be necessary some months later, this second apparatus becoming in turn, the preform for the third, etc. The transformations shall therefore be rapid since it is not necessary to start from scratch each time, unlike present day practices.

The process of the invention also allows the anchoring position of the fastening hooks to be moved slighting in the apparatus at the time of installation in the mouth and/or during treatment, thus, in some cases, avoiding the manufacture of a new apparatus.

Other characteristics and advantages of the invention shall be better understood by reading the description which follows, referring to the included figures in which:

BRIEF DESCRIPTION OF THE DRAWINGS

FIG. 1A shows a frontal cross-section (A-A axis), a preform without opening pursuant to the invention, adapted to obtain Bonnet's N.L.E.

FIGS. 1B and 1C show this preform respectively in a sagittal cross-section (longitudinal vertical) (B-B axis) and horizontal longitudinal cross section (C-C axis)

DETAILED DESCRIPTION OF THE INVENTION

Figure 2A:
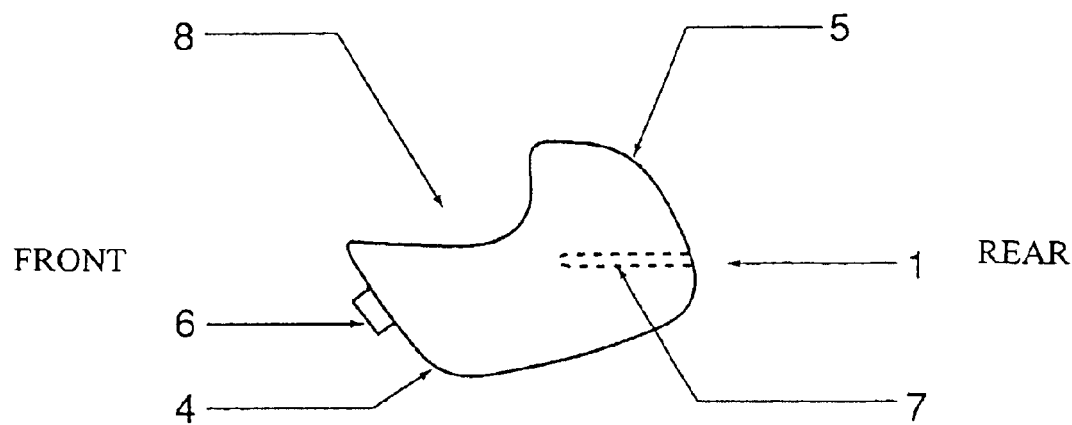
FIG. 2A shows a side view of a preform according to the invention, provided with an opening.
Figure 2B:
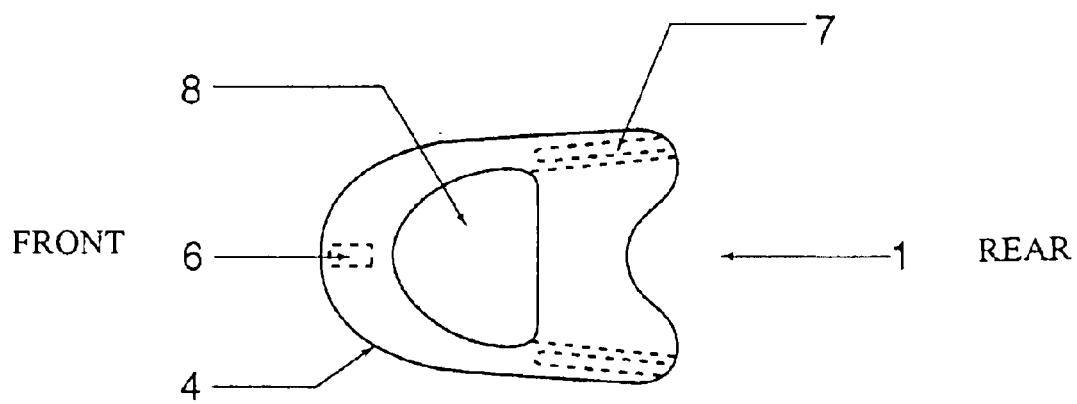
FIG. 2B shows the preform in 2A seen from above.
Figure 2C:
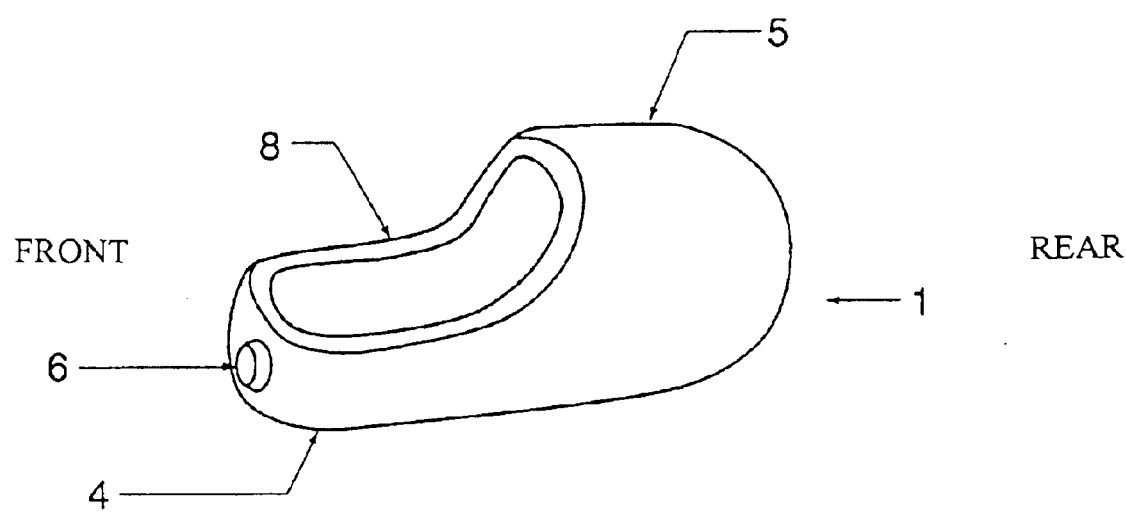
FIG. 2C shows a perspective view of the preform in 2A.

FIGS. 1 and 2 describe preforms (1) according to the invention, adapted to obtain Bonnet's N.L.E.

The preforms pursuant to the invention may have varying shapes, depending on the function of the shape of the apparatus obtained from the deformation of said preform. Furthermore, certain adaptations that are necessary in order to obtain a functional apparatus may be performed either at the preform stage or during the stage known as second stage processing, or after this stage. These adaptations may be made by cutting, machining, hot welding, or other processes. In a general manner, the preform has a shape that is as close as possible to the final form desired after deformation, in order to limit the number of operations to be performed by the practitioner or prosthesis maker all the while allowing a mass manufacture of the preform from the start. In one variation, the preform contains at least one opening.

FIG. 1 shows a preform (1) pursuant to the invention, with a hollow approximately tubular shape, without opening, having one utilizable extremity (2) and one non-utilizable extremity (3), said non-utilizable extremity being eliminated after the second stage processing of the preform into an apparatus adapted to the patient.

FIG. 2 describes another preform (1) according to the invention. This preform has an approximately tubular, hollow shape that is cut on the upper anterior part in order to form an opening (8). In the apparatus, this opening (8) is intended to allow the patient's tongue to touch the front of the palate, in particular the palatine papillae. This opening is made prior to second stage processing, but it is also possible to make it after second stage processing. The preform may also eventually contain an excrescence (6) intended to wedge the preform in the mechanism made for carrying out the second stage processing, as well as initial holes (7) used to hold the fastening hooks of the functional apparatus in the mouth. The area (5) corresponds to the palate, and the area (4) to the lower part or slide of Bonnet's N.L.E.

In the entire description, spatial coordinates are given in reference to an orthodontic or dento-facial orthopedic apparatus worn by a standing individual. The terms lower, anterior, posterior, etc. are therefore explicit. The cross-sectional planes are themselves also made in reference to an individual theoretically wearing the apparatus, or by extension, the preform, even the controllable expansion core defined later which, at rest, has the same shape as the preform. A frontal cross-section is a cross-section of the frontal plane of this individual, a saggital cross-section is a cross-section perpendicular to the first in the vertical plane (vertical axis of symmetry), finally a horizontal longitudinal cross-section is a cross-section perpendicular to the frontal cross-section, but this time in the horizontal plane.

The invention also concerns the process for transforming said preform.

The transformation of the preform shall allow, after any adaptation (preparation of opening, initial holes, fastening of additional pieces, anchoring of fastening hooks, reduction of the surface in certain areas, hollows, polishing, etc.) the production of a functional apparatus. Certain areas of this apparatus shall be adapted precisely to the specific morphology of the patient, others shall respect the shapes defined by the rules of the art of orthodontics with respect to the shape of the oral cavity.

In the present case, area (5) which corresponds to the palate, must be precisely adapted to the patient's morphology. However, area (4) which corresponds to the lower part, that is, the part retreating from the lower maxilla, and the lateral areas, retreating from the gums and teeth, are the areas defined by the rules of the art rather than by the patient's morphology.

Figure 3:
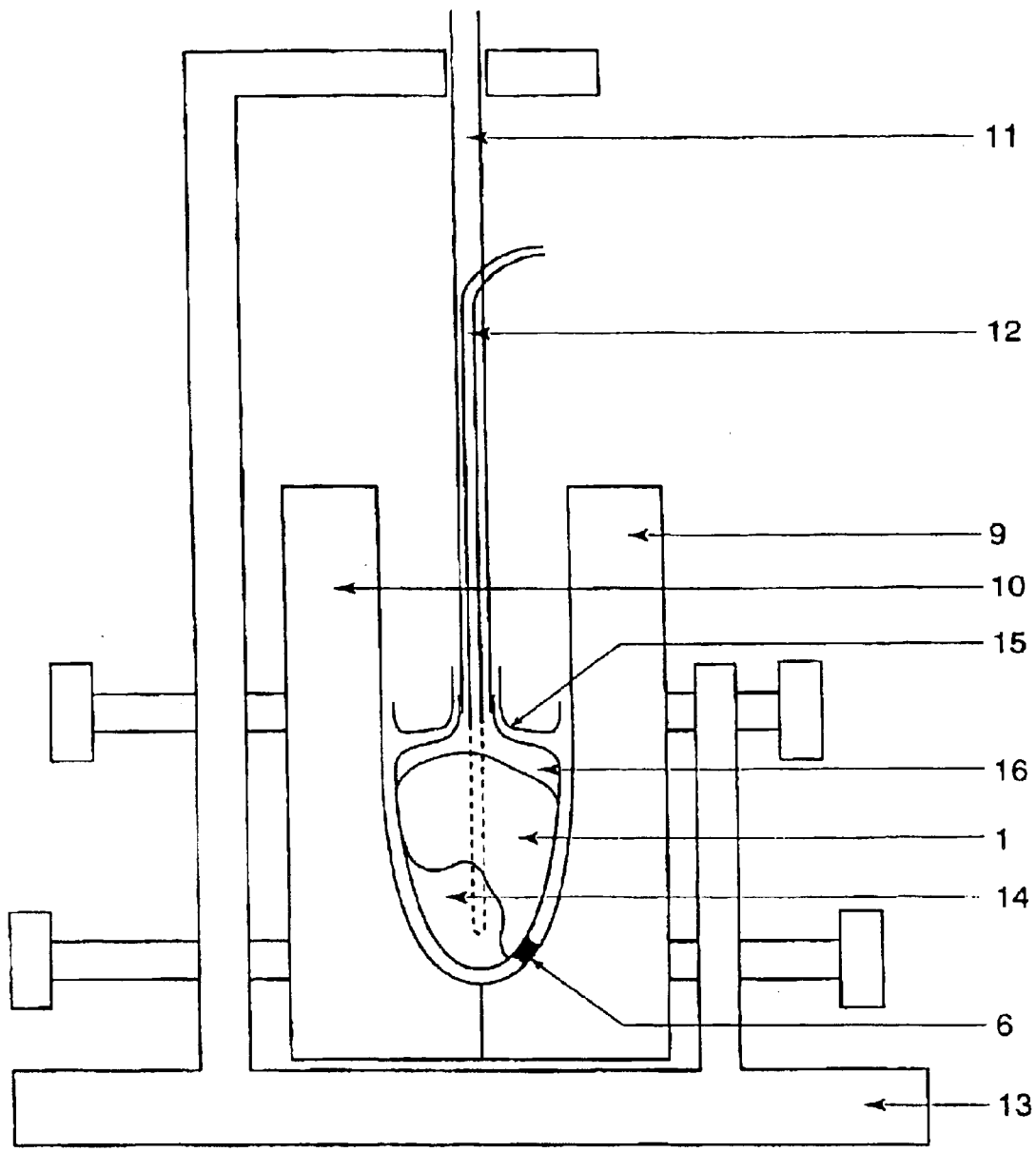
FIG. 3 shows a mechanism for the transformation of a preform into a functional apparatus following the patient's morphology.
Figure 4:
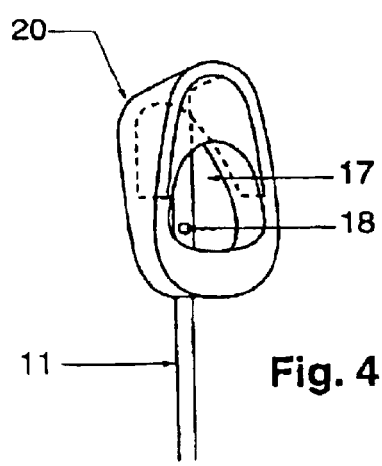
FIG. 4 shows a cross-section of a controllable expansion core used in a process according to the invention.
Figure 5A:
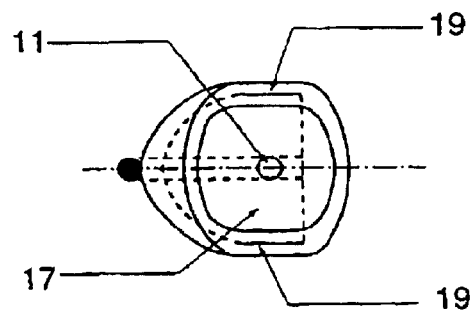
FIGS. 5A, 5B and 5C show the core from FIG. 4 in cross-sections that are respectively frontal, longitudinal horizontal, and saggital (longitudinal vertical)
Figure 5B:
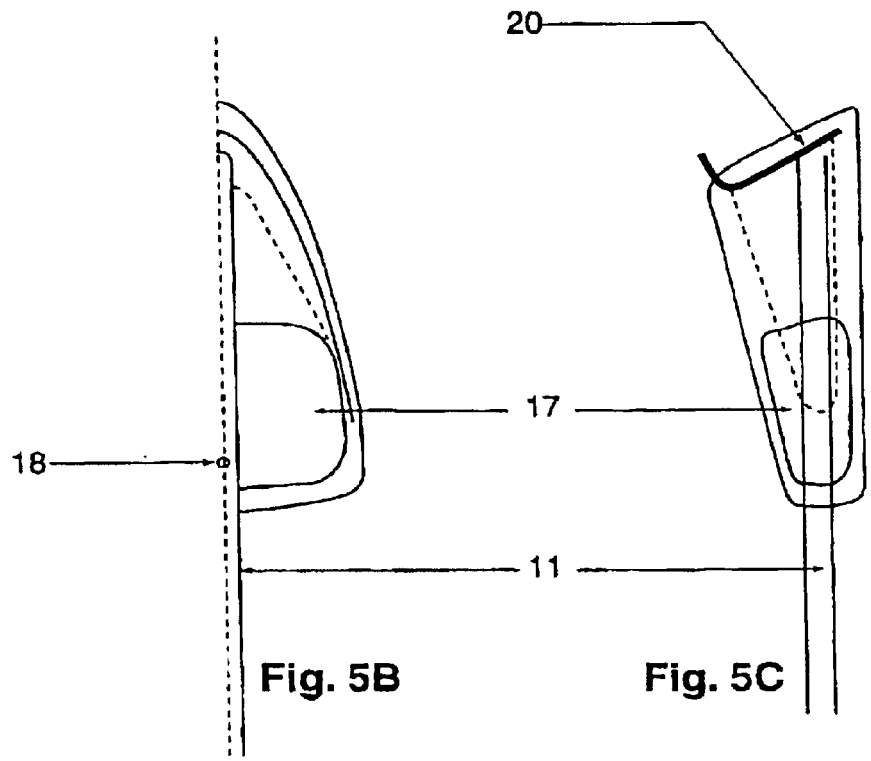
Figure 5C:
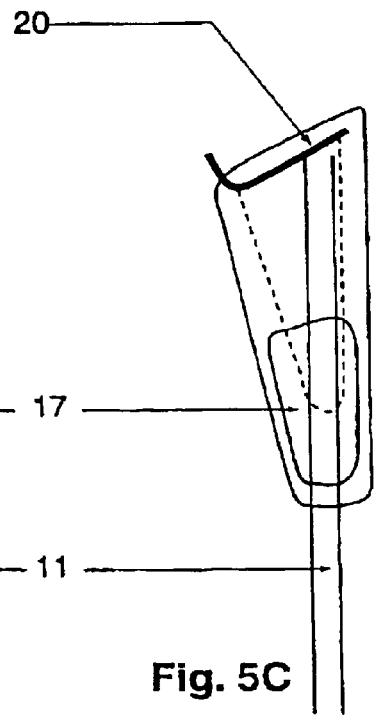

FIG. 3 shows the mechanism allowing second stage processing of the preform so as to eventually obtain a functional apparatus, after adaptation (preparation of an opening, reduction in the surface of certain areas, etc.), and prior to installation in the mouth by the practitioner.

This mechanism includes a female mold (or a female mold system) made up of models (9, 10) generally in plaster of the patient's upper maxilla and lower maxilla. In order to create these plaster models, the impression or impressions made by the practitioner of the patient when he examined the case are used as a matrix. This mold may be completed or modified by the traditional mechanical means (machining, addition of metallic pieces, stuffing with flexible material, for example silicone in plates or strips of varying width, length, and thickness adjusted to control the space left free between the expanded apparatus and the patient's oral cavity, or other) so as to have, where necessary, interior shapes defined by the rules of the art rather than the patient's morphology.

The plaster models (9, 10) constituting the female mold are maintained solidly and precisely in position with respect to each other in natural occlusion or in the relative position chosen by the practitioner and defined for example by a "bite" on wax or by marking of models, by a fastening system (13), for example a mechanical system, so as to constitute the second stage processing mold. The lock system may also fulfill the function of support and orientation with respect to the vertical of the ensemble.

The preform (1) is placed in the female mold (9, 10).

It may be modified prior to second stage processing to give it a morphology more favorable to obtaining the final form, such as for example, by creating an opening. All modifications or adaptations which can be performed prior to second stage processing will limit the number of operations after second stage processing.

Second stage processing depends on the material used for the manufacture of the preform. It includes deformation by expansion of the preform in order to obtain an apparatus adapted to the patient's morphology and to the rules of the art of orthodontics.

More precisely, it includes the following stages:
creation of a female mold based at least in part on the study models made from castings (in general with alginates) made by the practitioner of his patient,
positioning of the preform in the female mold,
expansion of the preform until it has reached the desired volume,
ejection from the mold of the apparatus which becomes functional after finishing.

Regardless of the material used, the process includes a main stage of expanding the preform. When a thermosetting product is used, the process also includes a polymerization step prior to ejection from the mold, The expansion may be performed with heat. In this sort of process, the preform is brought to the temperature for deformation of its constitutive material before the expansion stage, either after or before the positioning stage in the female mold.

It should be emphasized that the step of bringing the preform to the temperature for expansion and the expansion step are not necessarily performed in the same mechanism. It is, for example, possible to bring the preform to the expansion temperature in an oven then move it to the mold for expansion.

The preform is brought to the expansion temperature by the action of radiation (for example, in an oven, for example, an infrared oven) or a heat carrying fluid provided by a tube (12). The radiation used may also be of the microwave or ultraviolet type. The heat carrying fluid may, for example, be water brought to 100° C. In one production mode, the heat carrying fluid mixes with the expansion fluid.

The expansion may take place through the intermediary of an expansion fluid, for example compressed air or water, or even mechanically, until the preform has attained the desired shape, that is, until it is pressed at least in part against the inside of the mold. The expansion may also be limited by a controllable expansion core such as is described later. In this case, the expansion shall be controlled both by the mold (in certain parts) and by the controllable expansion core (in other parts).

The expansion may be performed by any method which allows the preform to take on the desired shape. This means may be a mechanism for expansion by movement of mechanical pieces changed by the technician during the expansion phase. In another method of production, expansion takes place through the inflating of an expansion core (14) presenting an empty space (17) within, placed beforehand inside the preform (1) and inflated by an expansion fluid. This core may be made of an elastomer material or any other material resistant to the expansion temperature. In the case depicted here, the core is held in position during expansion by a retaining plate (15) contiguous with the feed tube of the expansion fluid (for example, compressed air) (11) itself attached to the support (13). The end of the preform may be held in position by the intermediary of the excrescence (6) or by a part of the expansion core (14).

Such an expansion core may be produced by injection of an elastomer that is resistant to the expansion temperature, such as, for example, silicone, polyurethane, or nitrile. Production of the injection mold is based in traditional techniques that are not described in detail here. For example, it is possible to use injection or liquid silicone in a mold, for example, made of Plexiglas (for better visibility) containing a primary core of paraffin that is then eliminated with heat after cold curing or polymerization; or still by dipping with a primary core equipped with reinforcements, that is to say, without a mold. The primary core shall necessarily be meltable or destructible in order to create the necessary space (17) in the expansion core.

The expansion core may be a simple spherical or cylindrical shape of even thickness, but an evolved core or a controlled expansion core may also be used. Such a controlled expansion core is described in FIGS. 4 and 5A to 5C.

This evolved core (16) contains at least one means for controlling its expansion, for example, an increase in the thickness of its wall in certain areas and/or introduction in its wall of rigid reinforcements, for example, made of metal.

Preferably, such a core at rest would have the precise shape of the preform. It would thus allow the prehension of this preform and its movement and rapid positioning during handling, specifically during heat induced expansion, between bringing it to the expansion temperature and the expansion, that is to say, when the preform is hot.

Bringing it to the expansion temperature may therefore be performed on the preform alone (outside of the mold) for example, in an oven and for example by infrared radiation, and may be selective, that is to say, favoring the areas which are to undergo high expansion. In the case of Bonnet's N.L.E., the areas undergoing the strongest deformations, therefore those that shall be heated the most, are the upper edge of the slide and the upper posterior part of Bonnet's N.L.E. (which will touch the patient's palate).

The core may also contain metallic reinforcements such as spring bands (19) which, in some areas, will allow better control of deformations undergone by the preform. We refer to "controlled expansion", meaning anisotropic expansion. The expansion of the preform itself shall therefore be controlled at least in part by the core and not solely by the mold. Thus the core may replace the mold in the areas which must respect the rules of the art rather than the exact morphology of the patient: in these areas, the metallic reinforcements shall aid in the prevention of some undesired deformations. This shall allow the molds to be simplified. The element (20) serves to maintain the preform in position during expansion.

Furthermore, the core may contain a rigid tube (11), for example, in stainless steel, pierced with one hole (18) which shall allow the expansion fluid to arrive.

So that because of these structural differences in relation to the spherical core, the role of the controlled expansion core is more complex than the preform's single expansion.

As an example, an evolved core used in the development of a Bonnet's N.L.E. could have the following characteristics: high thickness and metal reinforcement at the front of the slide, decreasing lateral thickness and elastic metallic reinforcement, inserted metal tube, high posterior thickness, low thickness above and below.

When the utilizable end of the preform is closed (FIG. 1), the expansion core is not needed. Compressed air arrives directly into the preform (1) from its open end (3) adapted to the compressed air feed tube (11) by a sealing mechanism for example, of the serflex variety.

When the preform is manufactured using a thermosetting material, expansion is accompanied simultaneously or afterwards by a polymerization triggering mechanism which may be, for example (i) an increase in the temperature of the expansion mold+preform+any ballonet system., or (ii) an electromagnetic source such as microwaves or ultraviolet radiation emitted by a source placed in the core or in the preform and powered from within the compressed air feed tube (11).

After expansion, which allows the preform to reach the desired shape, and eventually polymerization, the piece obtained is ejected from the mold by opening the sealing system. In the case of heat induced expansion, the assembly is cooled prior to the piece being ejected from the mold in order to solidify the obtained shape.

This piece may then be finished or machined by any traditional process, such as, for example, polishing, deburring, localized heating by microguns using hot air or other substances, in order to obtain a functional apparatus adapted to the patient. This stage of finishing is shorter than in traditional processes, since the piece obtained is already very close to the final shape precisely adapted to the patient.

In the case that the preform is closed, the opening(s) in the piece obtained are prepared after the second stage processing by cutting, and the useless parts are eliminated (window, non-utilizable extremity) or the surface of certain areas is reduced, then finishing is conducted as described previously.

Finally, if necessary, the anchoring of the fastening hooks or of any other additional piece is made in any initial holes planned in the preform, or holes that are pierced after second stage processing, then glued or welded into position.

As specified above, the invention allows for the same apparatus to be used either during treatment of the patient, or by evolving it according to changes in morphology; the first apparatus produced serves as a preform for the second, itself serving as preform for the third and so on and so forth. It is therefore no longer necessary to produce a new apparatus after each stage. At the same time, it is essential to plan for fastening hooks whose anchoring points may be moved over time as a function of the changes in the patient's morphology and therefore as a function of the changes in the apparatus.

One of the purposes of the invention is therefore to offer an orthodontic apparatus obtained by the process described, and based on the described preform, with fastening hooks with moveable anchoring points.

In the basic version of such an apparatus, that is to say, using a thermoplastic material, the best process for fastening is welding, performed using one and/or the other methods indicated below.

Welding or heat-driven insertion of hot melt plastics requires two complementary and simultaneous functions:
  heating which may be obtained by any appropriate means, for example, mechanically by ultrasound, or electrically using the Joule effect, and
  transmission of the insertion force in the apparatuses and eventually the mechanical positioning of the piece to be inserted during cooling.

Three processes (and their mechanisms) are described below in the version of heating by the Joule effect, which is easily applicable to hooks and wires made of stainless steel.

In all three cases the mechanism for supplying the electric heating energy also provides stable mechanical positioning. The supply of electric energy may be provided by a portable current generator hand held by the technician (for example an instantaneous soldering iron designed or regulated so as to deliver an intensity which provides the piece to be inserted with the adequate temperature (approximately 5 amperes, 200° C.)), containing a pair of rigid conductors. In another mode of production, it may contain a mechanism called a gun which mechanically holds a pair of rigid electric conductors connected by flexible conductors to a fixed generator. The extremities of the rigid conductors are set-up so as to transmit the desired mechanical forces exerted by the technician to the hook which is to be inserted.

The three mechanisms described differ in their method of transmission of the mechanical forces to the piece to be heated and anchored and therefore in the shape of the extremities of the rigid conductors.

1. Mechanism with two extremities in the shape of a fork or a forked mechanism.

In order to ensure that the hook does not slip the extremity of each conductor has a shape adapted to the diameter of the wire or to the shape of the piece to be inserted, that is to say, the fastening hook. This shape provides stability to the mechanism's fulcrum on the piece to be inserted regardless of the force to be transmitted. Such a shape may, for example be in the shape of a fork. Such a mechanism shall be referred to by the term "forked mechanism", Only thrust may be transmitted to the piece to be inserted.

At the end of insertion, the technician stops pushing, the electric circuit opens, heating stops, the piece is free in the locally melted plastic.

The excess melted matter collected on the surface may be removed or shaped with a spatula while still warm (for example, by a piece created or covered with PTFE or an other material that does not stick to plastic) by the technician to improve the mechanical strength and appearance of the insertion. In one variation the spatula work is performed with a spring mechanism eventually released by the technician at the same time as the heating current is cut.

In order to control the degree of freedom and to avoid instability in the piece which may turn around the axis defined by the two forks during insertion, it is preferable to have recourse to a supplementary action, for example, holding the emerged extremity during the operation.

In this production method, the contact areas of the piece are finally included and the piece cannot be recuperated or moved by the same process since electric contact is no longer possible without machining the apparatus to bare the contact areas and the system does not allow extraction forces to be exerted.

FIGS. 8 (8A and 8B) shows a the right lateral view of a Sahar's hook (25) inserted or anchored in an apparatus (35) according. to. the, the invention, more specifically, around a lateral area (24) of the apparatus near the occlusion plane. The hook (25) includes a segment to insert (28) and a zigzag (26). This zigzag is inserted in a hollow (27) in the area (24) of the apparatus (35).

FIGS. 9 (9A and 9B) shows a right lateral hook (25) before insertion or anchoring in the lateral area (24) of an apparatus (35) by a forked insertion mechanism. In the mode of production shown, the extremity of each rigid conductor (29) of the insertion mechanism has the shape of a fork (30).

2. Mechanism containing two extremities in the form of a clamp, the piece to be inserted (fastening hook) containing a bent-back segment.

The extremity of each conductor is prepared to clamp the piece to be inserted (for example using a clamping screw of the sort for an electric box, a micro screw or spring clamp, a micro three-jaw chuck, or any other mechanical system). In a complementary manner, the piece to be inserted contains a bent back segment which remains outside of the apparatus at the end of insertion and the two segments are clamped by the mechanism. This type of hook is referred to by the term "hooks with bents back segments", At the end of insertion, the technician cuts the current (for example, using the trigger of the gun), the piece remains held by the mechanism which continues to clamp the piece, the positioning of the piece may therefore be adjusted precisely in all degrees of freedom during the cooling phase.

The excess melted matter collected on the surface may be removed or worked with a spatula as described previously.

Finally the two extremities of the inserted piece are freed by the opening of the clamps and remain emerging from the apparatus. They are, of course, designed and/or finished following traditional methods (loop or end loop) so as not to injure or bother the patient.

It is therefore possible to reposition the gun again later, to clamp the piece to make electric contact, to heat the piece and slightly move it in the apparatus. This facilitates adjustment of the installation in the mouth and the slight displacement, even replacement, of the hook for later follow-up care of changes in the patient's morphology.

These hooks with bent back segments, the process and the corresponding mechanism are quite appropriate for rear hooks since it is very useful to be able to move them or replacement during the life of the apparatus as was explained above.

FIGS. 10 (10A, 10B, and 10C) shows a rear right hook (25) with a bent back segment inserted in an apparatus (35) according to the invention, in one part of the apparatus with sufficient thickness, in general, close to the plane of occlusion. This hook with a bent-back segment has a primary segment (31) forming a contour along the teeth, an area (32) of pressure of the hook on the teeth, as well as a bent back segment (33) at the end, formed in a loop. Between the primary segment (31) and the bent back branch (33) lies the area (34) of the hook (25) which is inserted in the apparatus (35).

3. Mixed weld

In this case, each extremity of the mechanism is prepared following one of the above mechanisms, that is to say with fork and clamp. This process is generally quite appropriate for lateral Sahar's hooks. In effect, this configuration allows good handling of the piece to be inserted by the clamped segment and to completely insert the other segment.

The fastening hooks or complementary pieces can also be anchored during the second transformation, where it is the expansion itself that creates anchoring overmoldings, fastening hooks or complementary In one variation, the preform is manufactured and delivered to the technician in the developed form, that is, in two dimensions. This is a developed preform.

Figure 6:
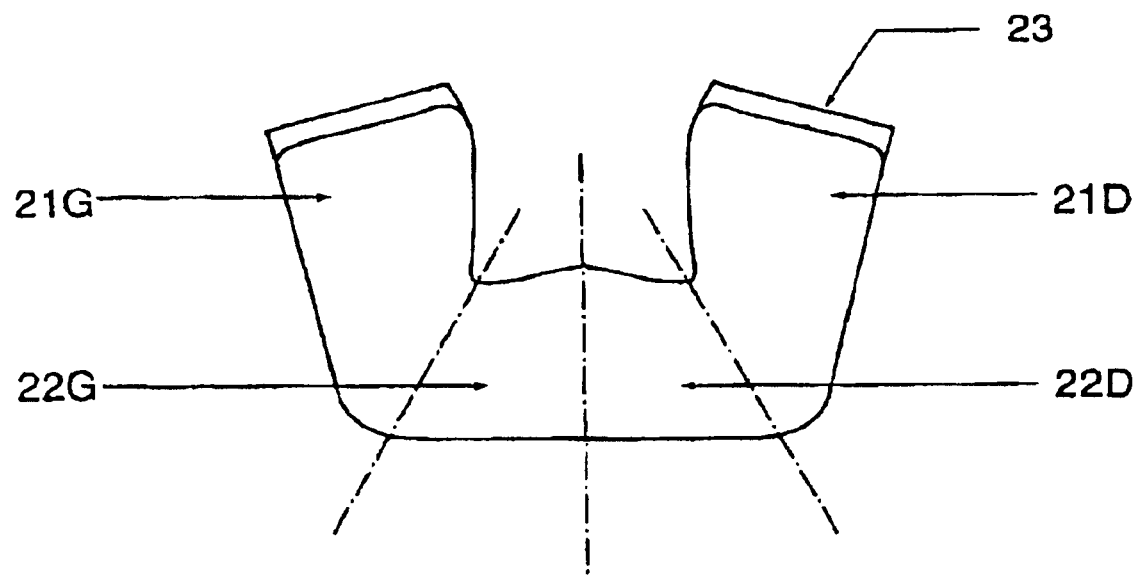
FIG. 6 shows a developed preform according to the invention.

FIG. 6 describes one such developed preform adapted to obtain a bonnet's N.L.E.. Area 21 is the semi-developed half of 21G or right 21D of the taper of the slide, area 22 is the semi-developed left 22G or right 22R of the palate. Areas 23 constitute the bow of the slide. The dotted lines represent the right, left and central (axis of symmetry) axes for bending.

Figure 7:
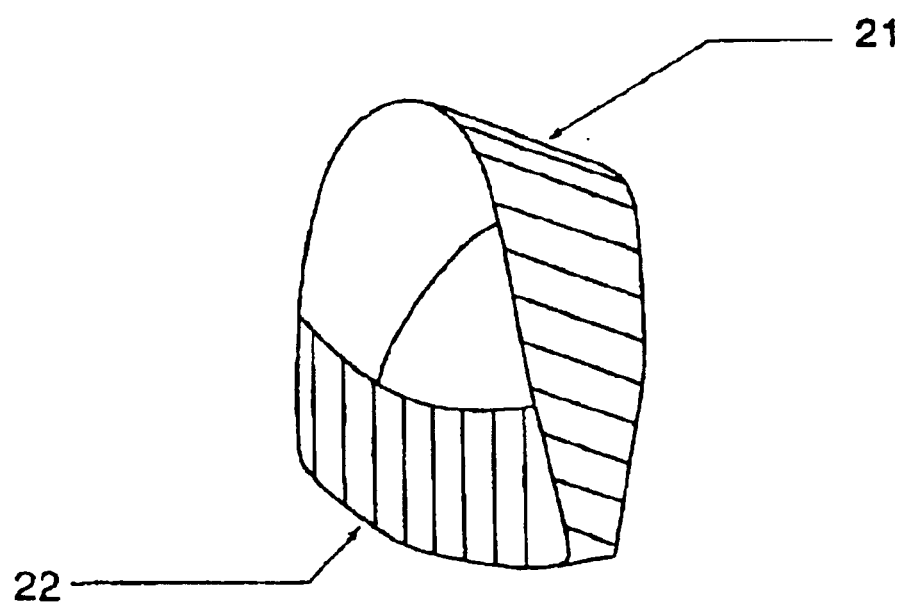
FIG. 7 shows[1] the preform obtained by rolling/bending of the developed preform in FIG. 6, FIGS. 8 (8A+8B) shows a right Sahar's hook inserted or anchored in an apparatus according to the invention (seen from behind and seen from the right), FIGS. 9 (9A+9B) shows a right lateral hook before anchoring in an apparatus according to the invention by a hook anchoring mechanism containing two fork-shaped extremities (seen from the left and seen from above), FIGS. 10 (10A+10B+10C) shows a right rear hook with returning forks inserted and anchored in an apparatus according to the invention (seen from the rear,se the left, and seen from above).

The developed preform is then given volume by the technician to create the preform as such shown in FIG. 7. The taper of the slide 21 and the palate 22 can be seen. The dotted line represents the right axis of bending. The connection (cross-section) to create the hollow body is located in the area that is least deformed during expansion, on the bow 23 of the slide 21 in this case of Bonnet's N.L.E. The weld is performed by hand pressure (self-adhesive effect) such that it then resists expansion.

This invention also concerns personalized orthodontic or dento-facial orthopedic apparatuses obtained by said transformation process starting with said preform. In a special case, such an apparatus is a Bonnet's Nighttime Lingual Envelope or N.L.E.

This invention covers the different adaptations, applications and modes of implementation which may be considered and which are known by people in the trade.

Thus, it is possible to produce several types of preforms, with different shapes and thicknesses which may be easily adapted to the desired function, to the size and morphology of patients (adults, children, etc.) and to the deformations that the preform shall undergo during second stage processing.

Similarly, the initial holes created to receive the fastening hooks when necessary may be eliminated or replaced by other mechanisms or arrangements (for example, impressions) facilitating the insertion of fastening pieces (bars with holes or pins) during (via duplicate molding) or after (gluing, screwing, welding, etc.) second stage processing.

The preform's surface may include guides, such as bumps or hollows intended to guide the technician during cutting operations, before or after second stage processing (preparation of the window, reduction of the surface in certain areas, etc.).

The material chosen to produce the preform may vary. In the case of thermoplastic material, it is possible, for example, to use polyethylene, polypropylene, methyl polymethacrylate or any other appropriate material. With regards to the use of this kind of thermoplastic material, we should refer to M. AMORIC's above mentioned work. In the case of thermosetting polyurethanes or methyl polymethacrylate or any other appropriate material may be used.

It is possible to use different colors or loads, even different flavors to make the use more attractive especially for young patients.

The preform may, in some parts, in particular in the areas where the surface geometry is determined by the rules of the art and not by the patient's morphology, have the definitive shape of the functional apparatus. For example, in the case of Bonnet's N.L.E., the lower part or slide has a shape close to that of the body of a cone.

The female mold may be created from a single model of the upper maxilla as first half-mold, and by an assembly of pieces having standard shapes following orthodontic rules or specific to the patient for the second half-mold. The controlled expansion core can also act as a mold in some areas.

Heating of the preform may take place by several processes; for example, hot air or other gas, hot liquid, electromagnetic radiation (such as infrared, microwaves or ultraviolet) emitted by a source external to the core or powered internally by the air feed tube.

The flow of the heat bearing fluid, which may be the expansion fluid, may be external to the preform and/or internal by using the fluid feed tube and a second tube inside of the first for the outflow. The same is true for cooling after transformation.

What is claimed is:

1. A preform with a hollow tubular or approximately tubular shape for obtaining, after deformation, a personalized orthodonic or dentofacial orthopedic apparatus that can be expanded inside a mold reproducing the morphology of a subject, wherein said preform has a variable thickness and is cut on an upper anterior part thereof to form an opening, leaving a closed upper posterior part while a lower part or slide is adapted to substantially match a lower maxilla of the subject.

2. The preform according to claim 1, wherein the preform is formed from a biocompatible material.

3. The preform according to claim 1, comprising a thermoplastic or thermosetting plastic material which is deformable through expansion.

4. The preform according to claim 3, comprising a thermoplastic material selected from the group consisting of polyethylene, polypropylene, polycarbonate, methyl polymethacrylate, PVC, and polyurethane, or a thermosetting plastic material selected from the group consisting of methyl polymethacrylate and polyurethane.

5. The preform according to claim 1, characterized by a surface with guides comprising bumps or recesses intended to guide a technician during cutting operations and/or initial holes for holding fastening hooks of the dentofacial apparatus.

6. The preform according to claim 1, comprising a flat, developed shape prior to shaping by a technician.

7. The preform according to claim 1 for obtaining after deformation, a Bonnet's Nighttime Lingual Envelope (N.L.E.), that can be expanded inside a mold reproducing the morphology of a subject, wherein said preform has a hollow shape that is cut on the upper anterior part in order to form an opening, wherein said preform has an area corresponding to the palate and to an area to the lower part or slide of the N.L.E.

8. A process for manufacturing a personalized orthodontic or dento-facial orthopedic apparatus, comprising:
   a) providing a female mold based at least in part on study models created by a practitioner from a casting or castings made from a subject,
   b) positioning a preform of claim 1 in the female mold,
   c) expanding the preform to obtain the apparatus having a desired shape, and
   d) removing the apparatus from the mold and finishing the apparatus.

9. The process according to claim 8, wherein the expanding step of c) is preformed with heat and the preform is brought to a deformation temperature of its constitutive material prior to expansion.

10. The process according to claim 9, wherein an expansion temperature is attained by radiation or a heat bearing fluid.

11. The process according to claim 10, wherein the radiation is microwave, ultraviolet or infrared.

12. The process according to claim 8, wherein the expanding step of c) is preformed by a method for obtaining an expansion of the preform to a desired shape.

13. The process according to claim 12, comprising expanding by an expansion fluid or mechanically.

14. The process according to claim 13, wherein the expansion fluid is compressed air or water.

15. The process according to claim 8, wherein the expanding step of c) occurs by inserting an expansion core in the preform and inflating the expansion core with an expansion fluid.

16. The process according to claim 15, wherein the expansion core is a controlled expansion core.

17. The process according to claim 15, wherein the expansion core comprises a material resistant to an expansion temperature.

18. The process according to claim 17, wherein the material resistant to an expansion temperature is an elastomer.

19. The process according to claim 8, wherein the preform is made of thermosetting material and the expanding step of c) is simultaneously or later accompanied by a step for polymerization of the thermosetting material.

20. The process according to claim 8, further comprising inserting fastening pieces or additional pieces during the expanding step of c).

21. The process according to claim 8, wherein the finishing step of d) includes at least one of preparing one or more openings, polishing, anchoring of fastening hooks, setting of additional pieces, elimination of useless parts, or reduction of surface areas.

22. The process according to claim 21, wherein the finishing step of d) comprises anchoring the fastening hooks to moveable anchoring points on the apparatus.

23. The process according to claim 22, wherein the fastening hooks are attached using a fastening mechanism.

24. The process according to claim 21 wherein the finishing step of d) comprises anchoring the fastening hooks to an orthodontic or dento-facial orthopedic apparatus by means for supplying electrical heating energy and stable positioning of the fastening hook for anchoring to the apparatus.

25. The process according to claim 24 wherein the electrical energy is supplied by a hand-held, portable current generator.

26. The process according to claim 24 wherein the stable mechanical positioning is performed with the distal ends of electrical conductors having a clamp shape, and the distal ends are adapted to the diameter of a wire or to a shape of the hook to be inserted.

27. The process according to claim 24 wherein the electrical energy is supplied by a gun that mechanically holds a pair of rigid electrical conductors connected by flexible conductors to a fixed generator.

28. The process according to claim 8, wherein the dento-facial orthopedic or orthodontic apparatus obtained by the process of a preceding cycle, is used as the preform.

29. The process according to claim 8, wherein the personalized orthodontic or dento-facial orthopedic apparatus is a Bonnet's Nighttime Lingual Envelope (N.L.E.).

30. A method of manufacturing a personalized orthodontic or dento-facial orthopedic apparatus, comprising:

a) providing a female mold based at least in part on study models created by a practitioner from a casting or castings made from a subject, b) positioning a preform in the female mold, c) expanding the preform with an expansion mechanism so as to obtain an apparatus having a desired shape by displacement of mechanical pieces on the expansion mechanism, and d) removing the apparatus from the mold and finishing the apparatus, wherein the preform comprises a three-dimensional hollow body with a form allowing expansion of the preform inside a mold reproducing a morphology of a subject.

31. An orthodontic or dento-facial orthopedic apparatus manufactured according to a process comprising:

a) providing a female mold based at least in part on study models created by a practitioner from a casting or casting made from a subject, b) positioning a preform comprising a thermoplastic material in the female mold, c) expanding the preform so as to obtain an apparatus having a bent-back segment for inserting the fastening hook, and d) removing the apparatus from the mold and finishing the apparatus and comprising one or more fastening hook, wherein a fastening hook is inserted into the bent-back segment of the apparatus.

* * * * *

UNITED STATES PATENT AND TRADEMARK OFFICE
CERTIFICATE OF CORRECTION

PATENT NO.    : 6,832,914 B1
DATED         : December 21, 2004
INVENTOR(S)   : Maïwenn Bonnet et al.

It is certified that error appears in the above-identified patent and that said Letters Patent is hereby corrected as shown below:

Title page,
Item [76], Inventors, please correct to read as follows:
-- Maïwenn Bonnet, 66 rue Daguerre, 75014 Paris (FR); François Bonnet, 27 allee des Thuyas, 44500 La Baule, (FR); Bruno Bonnet, 12 rue Danton, 94270, Le Kremlin Bicetre (FR) --.

Signed and Sealed this

Eleventh Day of October, 2005

JON W. DUDAS
*Director of the United States Patent and Trademark Office*